United States Patent [19]

Cosmescu

[11] Patent Number: 5,318,516
[45] Date of Patent: Jun. 7, 1994

[54] RADIO FREQUENCY SENSOR FOR AUTOMATIC SMOKE EVACUATOR SYSTEM FOR A SURGICAL LASER AND/OR ELECTRICAL APPARATUS AND METHOD THEREFOR

[76] Inventor: Ioan Cosmescu, 14449 No. 22nd St., Pheonix, Ariz. 85022

[21] Appl. No.: 989,237

[22] Filed: Dec. 11, 1992

Related U.S. Application Data

[63] Continuation-in-part of Ser. No. 714,842, Jul. 24, 1991, Pat. No. 5,199,944, which is a continuation-in-part of Ser. No. 527,589, May 23, 1990, Pat. No. 5,108,389.

[51] Int. Cl.⁵ .............................................. A61B 17/39
[52] U.S. Cl. .......................................... 604/35; 606/10; 606/34; 606/38; 606/45
[58] Field of Search .............................. 604/21, 23-28, 604/30, 35; 606/10, 13, 14, 34, 35, 37-42, 45; 219/121.84, 137.41

[56] References Cited

U.S. PATENT DOCUMENTS

| | | | |
|---|---|---|---|
| 4,207,887 | 6/1980 | Hiltbrandt et al. | 604/26 |
| 4,648,386 | 3/1987 | Morritt et al. | 604/25 |
| 4,715,372 | 12/1987 | Philippbar et al. | 606/10 |
| 4,719,914 | 1/1988 | Johnson | 606/45 |
| 4,735,603 | 4/1988 | Goodson et al. | 604/35 |
| 4,735,606 | 4/1988 | Davison | 604/28 |
| 4,850,352 | 7/1989 | Johnson | 604/35 |
| 4,931,047 | 6/1990 | Broadwin et al. | 606/45 |
| 4,966,578 | 10/1990 | Baier et al. | 604/26 |
| 4,971,034 | 11/1990 | Doi et al. | 606/10 |
| 5,013,294 | 5/1991 | Bair | 604/26 |
| 5,085,657 | 2/1992 | Ben-Simhon | 606/42 |
| 5,088,997 | 2/1992 | Decahuerga et al. | 606/45 |
| 5,108,389 | 4/1992 | Cosmescu | 606/10 |
| 5,160,334 | 11/1992 | Billings et al. | 606/34 |
| 5,199,944 | 4/1993 | Cosmescu | 604/26 |

*Primary Examiner*—Ralph Lewis
*Attorney, Agent, or Firm*—Harry M. Weiss

[57] ABSTRACT

A laser surgical apparatus having an improved smoke evacuator system and method is provided whereby the radio frequency energy associated with the generation of RF from the electrosurgical unit (ESU) or a laser surgical apparatus is detected by a radio frequency sensor which in turn generates a control signal which provides the automatic control that activates the automatic smoke evacuator system only during the approximate period of time when the laser surgical or electrosurgical unit is being utilized for surgical procedures.

16 Claims, 1 Drawing Sheet

RADIO FREQUENCY SENSOR FOR AUTOMATIC SMOKE EVACUATOR SYSTEM FOR A SURGICAL LASER AND/OR ELECTRICAL APPARATUS AND METHOD THEREFOR

Related Application

This patent application is a continuation-in-part of my earlier patent application entitled "RADIO FREQUENCY SENSOR FOR AUTOMATIC SMOKE EVACUATOR SYSTEM FOR A SURGICAL LASER AND/OR ELECTROSURGICAL APPARATUS AND METHOD THEREFOR", Ser. No. 07/764,842, filed Sep. 24, 1991, now U.S. Pat. No. 5,199,944, which is a continuation-in-part of application Ser. No. 07/527,589, filed May 20, 1990, now U.S. Pat. No. 5,108,389, and incorporated by reference thereto.

BACKGROUND OF THE INVENTION

1. Field of the Invention

This invention refers in general to automatic smoke evacuator system and methods therefor for laser and electrosurgical apparatus and, in particular, to automatic smoke evacuator systems and methods therefor for a laser surgical apparatus and an electrosurgical unit (ESU) in which the radio frequency (RF) energy which is necessarily associated with the operation of the laser surgical apparatus and ESU is detected by an RF sensor which then actuates the operation of the automatic smoke evacuator system.

2. Description of the Prior Art

In the past, a surgical laser apparatus utilized a smoke evacuator system which was manually turned on and off, but which was generally continuously operated during a surgical laser procedure. A smoke evacuator system functioned with a surgical laser apparatus. The smoke evacuator systems produced a constant noise during its use or operation, used a high amount of electrical energy and the continuous air pressure on the filter element of the smoke evacuator systems usually saturated or overloaded the system's filter thereby increasing the risk of allowing toxic fumes which were supposed to be evacuated from the surgical area to escape uncontrolled into the medical operating room rather than being vented outside in accord with the intended function of the smoke evacuator system. Further, for safety purposes, the FDA does not allow any device to be in electrical contact with the control circuitry of a surgical laser. Therefore, there was clearly great benefit to the surgeon and to the operating room staff if the smoke evacuator systems was activated only during the period of time the laser surgical apparatus was actually in Operation. My U.S. Pat. No. 5,108,389 provides a solution to these problems of past systems by Providing an automatic smoke evacuator system in which the required activation of the smoke evacuator is initiated by the interruption of a beam of electromagnetic radiation. In the preferred embodiment, the beam of electromagnetic radiation is an infrared beam which is interrupted by a foot switch which is coupled to the laser ESU and which controls its actuation. As is described in U.S. Pat. No. 5,108,389, this system greatly improves the safety and effectiveness of the operating environment for laser surgical procedures and has provided great benefit in it use.

SUMMARY OF THE INVENTION

An object of this invention is to provide an improved smoke evacuator system and method for a laser surgical apparatus and ESU.

Another object of this invention is to provide an improved smoke evacuator system and method for a laser surgical apparatus and ESU which has an automatic control that activates the smoke evacuator system only during the approximate period of time when the laser surgical unit and/or ESU is being utilized for surgical procedures which is when the laser cutting beam of the laser surgical apparatus and/or ESU is on.

Another object of this invention is to provide an improved smoke evacuator system and method for a laser surgical apparatus and ESU which has an automatic control that activates the smoke evacuator system only during the approximate period of time when the laser surgical unit is being utilized for surgical procedures which is when the laser cutting beam of the laser surgical apparatus or the RF of ESU is on such that the radio frequency energy associated with the generation of the RF laser tube of the laser surgical apparatus or ESU is detected by a radio frequency sensor which in turn generates a control signal which provides the automatic control that activates the smoke evacuator system only during the approximate period of time when the laser surgical unit and/or ESU is being utilized for surgical procedures.

It is still another object of this invention is to provide an improved smoke evacuator system and method whereby the radio frequency energy associated with the generation of the RF laser cutting power supply P.S. of the laser surgical apparatus or ESU is detected by a radio frequency sensor which in turn generates a control signal which provides the automatic control that activates the smoke evacuator system only during the approximate period of time when the laser surgical unit and/or ESU is being utilized for surgical procedures which also has delay circuitry or means to allow the continued operation of the smoke evacuator system for a variable time Period (which is operator selected) after the laser cutting beam of the laser surgical apparatus is turned off in order to remove all of the toxic smoke from the operating room prior to the turn off of the smoke evacuator system.

According to the present invention, an improved smoke evacuator system and method is provided whereby the radio frequency energy associated with the generation of the RF laser P.S. of the laser surgical apparatus or ESU is detected by a radio frequency sensor which in turn generates a control signal which provides the automatic control that activates the smoke evacuator system only during the approximate period of time when the laser surgical unit or ESU is being utilized for surgical procedures.

The foregoing and other objects, features and advantages of the present invention, as well as details of the preferred embodiment thereof, will be more fully understood from the following description and drawing.

DESCRIPTION OF THE PREFERRED EMBODIMENT

Figure 1:
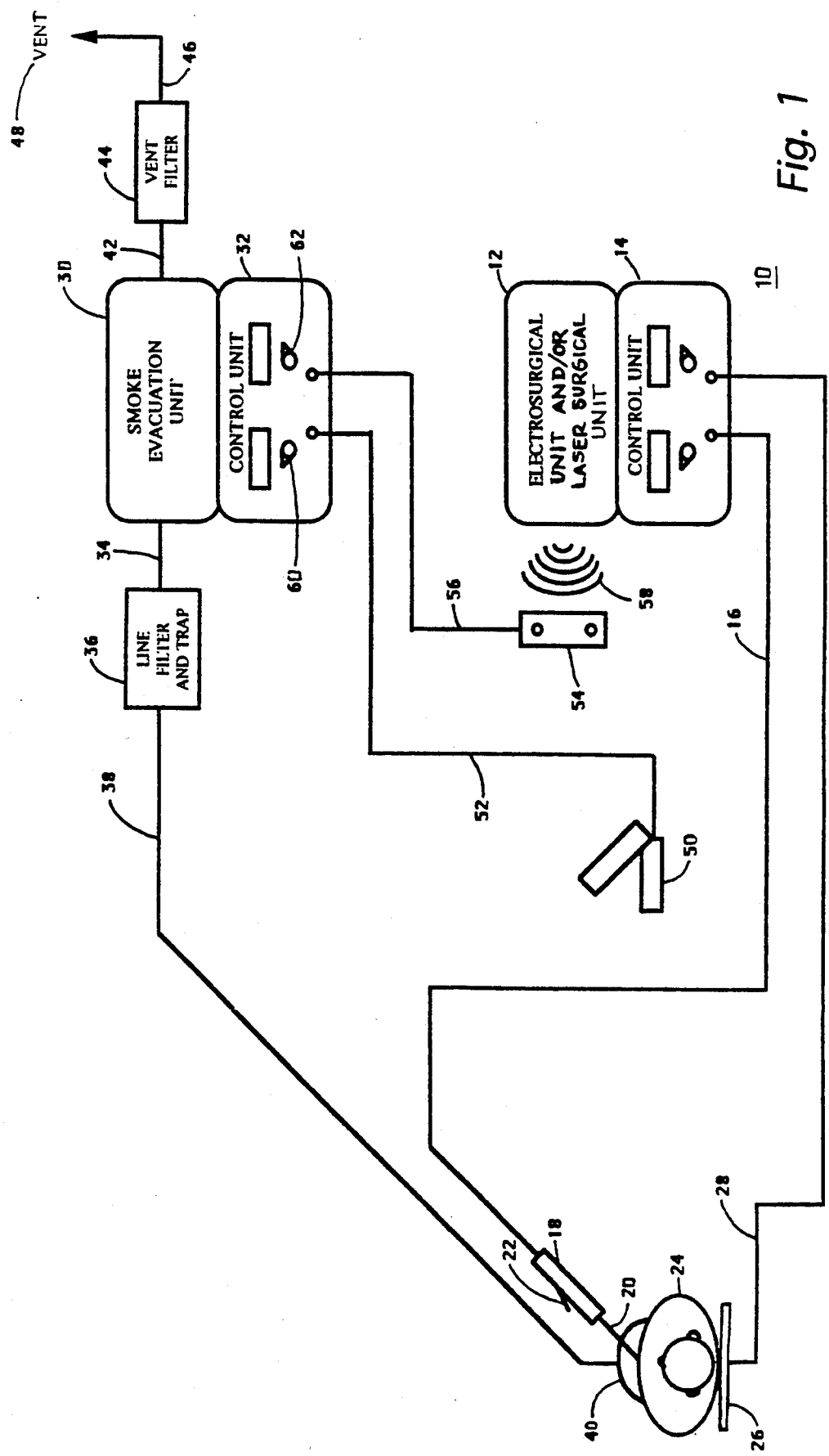
FIG. 1 is a block diagram of the automatic smoke evacuator actuator system for a surgical laser or ESU apparatus according to the present invention.

FIG. 1 is a block diagram of the automatic smoke evacuator actuator system for a surgical laser apparatus or ESU 10 according to the present invention. In the system of FIG. 1, a laser or electrosurgical unit (ESU) 12 which includes a control unit 14 produces a RF output signal which is coupled via output path 16 to an ESU hand piece 18 which has an operating tip 20 and has a control switch 22. Operating tip 20 applies RF energy to a surgical location on or within a patient 24 as required by the procedure underway. During this procedure, patient 24 is in contact with a patient ground plate 26 which couples to patient ground return path 28 which couples to control unit 14 of the laser or electrosurgical unit 12. The system of FIG. 1 also includes a smoke evacuator unit 30 which includes a control unit 32. Smoke evacuation unit 30 couples to smoke evacuation channel 34 which couples to line filter and fluid trap 36. Line filter and fluid trap 36 couples to smoke evacuation channel 38 which couples to smoke evacuation shroud means 40. Smoke evacuation shroud means 40 functions to provide a collection region for evacuating the plume of toxic smoke produced by the cutting action of operating tip 20 of ESU hand piece 18. Smoke evacuation unit 30 also couples to smoke evacuation channel 42 which couples to vent filter 44 which couples via smoke evacuation channel 46 to vent 48. Vent 48 provides means for evacuated toxic smoke to exit the operating room where the laser surgical procedure takes place. The system of FIG. 1 also includes a foot switch sensor means 50 which couples via first control channel 52 to an input of control unit 32 of smoke evacuation unit 30. The system of FIG. 1 also includes a radio frequency (RF) sensor 54 which couples via second control channel 56 to another input of control unit 32 of smoke evacuation unit 30. RF sensor 54 functions to respond to waves of RF energy 58 which are produced and radiated by the laser or electrosurgical unit 12. The waves of RF energy 58 are produced as "stray" or "leakage" energy when the source of RF energy which is used internal to the laser or electrosurgical unit 12 to provide the excitation energy required to operate the laser or ESU. Control unit 32 of smoke evacuation unit 30 also a first operating mode switch 60 and a second operating mode switch 62 which function to allow the first control channel 52 and the second control channel 56 to function independently or simultaneously.

The majority of the features of the operation of the system of FIG. 1 are those which have been already disclosed and described in my U.S. Pat. No. 5,108,389 for an automatic smoke evacuator activator system which is hereby incorporated by reference. As shown by the system diagram of FIG. 1, the operation of the system wherein a foot switch sensor means 50 which couples via first control channel 52 to an input of control unit 32 of smoke evacuation unit 30 to provide the required smoke evacuation for removal of toxic smoke is the same as in U.S. Pat. No. 5,108,389. The new features of the system of FIG. 1 are the addition of a radio frequency (RF) sensor 54 which couples via second control channel 56 to another input of control unit 32 of smoke evacuation unit 30. These additional features add a new and advantageous dimension to the overall operation of the system of FIG. 1 which further assist the surgeon as the laser or electrosurgical procedure is performed. As previously described, RF sensor 54 functions to respond to waves of RF energy 58 which are produced and radiated by the laser electrosurgical unit 12. The waves of RF energy 58 are produced as "stray" or "leakage" energy when the source of RF energy which is used internal to laser electrosurgical unit 12 to provide the excitation energy required to operate the laser. Thus when the surgeon energizes the ESU hand piece 18 by actuating control switch 22, the waves of RF energy 58 are instantaneously produced as the excitation energy required at operating tip 20. The surgeon now has multiple options for controlling the evacuation of toxic smoke from the laser surgery site. By making the appropriate adjustments to first operating mode switch 60 and second operating mode switch 62, the surgeon can obtain the most advantageous mode of smoke evacuation for the particular surgical location of interest by using only foot switch control, only RF sensor control or a suitable combination of both. A further adjustment which can be made by the surgeon is to use time delay features of control unit 32 of smoke evacuation unit 30 as disclosed in U.S. Pat. No. 5,108,389 which can be used to further enhance any of these operating modes of smoke evacuation.

While the invention has been particularly shown and described with reference to a preferred embodiment thereof, it will be understood by those skilled in the art that changes in form and detail may be made therein without departing from the spirit and the scope of the invention. For example, the RF sensor could be additionally used to control other equipment or instead of RF other frequencies of the electromagnetic spectrum can be used like accoustic waves.

I claim:

1. An automatic smoke evacuator system for a laser surgical apparatus comprising in combination:
   laser means for generating a surgical laser beam, said laser means having a RF excitation source;
   RF sensor means for sensing RF energy produced by said RF excitation source; and
   smoke evacuator system means having a first control input and a second control input for evacuating toxic smoke from a laser surgical site when actuated by said RF sensor means coupled to said first control input.

2. The automatic smoke evacuator system according to claim 1 further comprising:
   foot switch means coupled to said second control input for actuating said smoke evacuator system means.

3. The automatic smoke evacuator system according to claim 2, said smoke evacuator system means further comprising:
   mode control means for allowing said RF sensor means and said foot switch means to actuate said smoke evacuator system means independently.

4. The automatic smoke evacuator system according to claim 3, said smoke evacuator system means further comprising:
   time delay means for defining an interval of time; and
   delay control means for turning off said smoke evacuator system means said interval of time after the end of an actuating signal.

5. An automatic smoke evacuator system for one of a laser surgical and electrosurgical apparatus comprising smoke evacuation means and RF sensor means adaptively coupled to said smoke evacuation means for actuating said smoke evacuation means in response to the RF energy emanated by the RF excitation of said laser or electrosurgical apparatus.

6. An automatic smoke evacuator system for one of a laser surgical and electrosurgical apparatus according to claim 5 further comprising switch means adaptively coupled to smoke evacuation means for actuating said smoke evacuation means in response to manual control.

7. An automatic smoke evacuator system for one of a laser surgical and electrosurgical apparatus according to claim 6 further comprising control means adaptively coupled to smoke evacuation means for allowing said RF sensor means and said switch means to independently actuate said smoke evacuation means.

8. An automatic smoke evacuator system for one of a laser surgical and electrosurgical apparatus according to claim 7 further comprising time delay control means adaptively coupled to said smoke evacuation means for allowing said smoke evacuation means to turn off an interval of time after the end of an actuation signal.

9. A method for providing an automatic smoke evacuator system for one of a laser surgical and electrosurgical apparatus comprising the steps of:
   providing means for generating at least one of a surgical laser beam and electrosurgical arc, said means having a RF excitation source;
   providing RF sensor means for sensing RF energy produced by said RF excitation source; and
   providing smoke evacuator system means having a first control input and a second control input for evacuating toxic smoke from a surgical site when actuated by said RF sensor means coupled to said first control input.

10. The method of providing an automatic smoke actuator system according to claim 9 further comprising the step of:
   providing foot switch sensor means coupled to said second control input for actuating said smoke evacuator system means.

11. The method of providing an automatic smoke evacuator system according to claim 10, said smoke evacuator system means further comprising:
   mode control means for allowing said RF sensor means and said foot switch means to actuate said smoke evacuator system means independently.

12. The method of providing an automatic smoke evacuator system according to claim 11, said smoke evacuator system means further comprising:
   time delay means for defining an interval of time; and
   delay control means for turning off said smoke evacuator system me and said interval of time after the end of an actuating signal.

13. A method of providing an automatic smoke evacuator system for one of a laser surgical and electrosurgical apparatus comprising the step of providing RF sensor means adaptively coupled to smoke evacuation means for actuating said smoke evacuation means in response to the RF energy emanated by the RF excitation of said laser surgical or electrosurgical apparatus.

14. A method of providing an automatic smoke evacuator system for one of a laser surgical and electrosurgical apparatus according to claim 13 further comprising the step of providing switch means adaptively coupled for actuating said smoke evacuation means in response to manual control.

15. A method of providing an automatic smoke evacuator system for one of a laser surgical and electrosurgical apparatus according to claim 14 further comprising the step of providing control means adaptively coupled for allowing said RF sensor means and said switch means to independently actuate said smoke evacuation means.

16. A method of providing an automatic smoke evacuator system for one of a laser surgical and electrosurgical apparatus according to claim 15 further comprising the step of providing time delay control means adaptively coupled for allowing said smoke evacuation means to turn off an interval of time after the end of an actuation signal.

* * * * *